United States Patent [19]

Entis et al.

[11] 4,397,955
[45] Aug. 9, 1983

[54] TRANSFER APPARATUS FOR MICROORGANISMS

[76] Inventors: Phyllis Entis; Michael P. Entis, both of 135 The West Mall Unit 2, Etobicoke, Ontario, Canada, M9C 1C2

[21] Appl. No.: 247,259

[22] Filed: Mar. 25, 1981

[30] Foreign Application Priority Data

Nov. 21, 1980 [CA] Canada .................................. 365248

[51] Int. Cl.³ ...................... C12M 1/26; C12M 1/32; C12Q 1/24; C12M 1/00
[52] U.S. Cl. .................................... 435/292; 435/30; 435/287; 435/293
[58] Field of Search ................. 435/30, 292, 293, 294, 435/287, 291, 301, 311, 34; 23/230 B

[56] References Cited

U.S. PATENT DOCUMENTS

| | | | |
|---|---|---|---|
| 3,661,718 | 5/1972 | Sterling | 435/292 X |
| 3,684,660 | 8/1972 | Kereluk et al. | 435/294 |
| 3,694,317 | 9/1972 | Scher | 435/30 X |
| 3,729,382 | 4/1973 | Shaffer et al. | 435/294 |
| 3,897,688 | 8/1975 | Meserol et al. | 435/292 X |
| 3,929,583 | 12/1975 | Sharpe et al. | 435/301 |
| 4,237,223 | 12/1980 | Metz | 435/292 X |

*Primary Examiner*—David M. Naff
*Attorney, Agent, or Firm*—Riches, McKenzie & Herbert

[57] ABSTRACT

This invention relates to a transfer mechanism for microorganisms and more specifically, to a device for duplicating a growth pattern of microorganisms. The apparatus comprises a body and a transfer material on one surface of the body. The transfer material is brought into contact with a primary medium having a growth of microorganisms on the surface thereof, and transfers that growth to at least one secondary medium. The apparatus is particularly suitable for use with a hydrophobic grid membrane filter. This apparatus replaces slow and cumbersome methods for transferring microorganisms from a primary medium to a secondary medium and is an automated and efficient apparatus to effect such transfer. This device makes it now possible to transfer and duplicate the colonies of microorganisms growing on a hydrophobic grid membrane filter to fresh or different culture media.

21 Claims, 3 Drawing Figures

# 4,397,955

TRANSFER APPARATUS FOR MICROORGANISMS

BACKGROUND OF THE INVENTION

1. Field of the Invention

This invention relates generally to a transfer mechanism for microorganisms and more specifically, to a device for duplicating a growth pattern of microorganisms.

2. Description of the Prior Art

It is essential in many industries to be able to determine whether or not microorganisms are present in raw materials, finished products and intermediate products used and made in that industry, as well as by-products and effluent resulting from the industrial process, and also to be able to classify the microorganisms if present. Many such microorganisms are not only undesirable but some are detrimental to the health of the consumer of the product and thus prohibited by government regulation.

In addition to the need for detection and quantification of microorganisms in a sample, it is often essential to classify any microorganism so found into its proper taxonomic category.

This need exists for many industries, but it is particularly important for such industries as the drug industry, the food industry and the cosmetic industry. Government regulations in most jurisdictions strictly control the quantity of certain microorganisms which is permitted in food, drug, cosmetic and similar products, and accurate tests must be performed at regular intervals to ensure compliance with these regulations.

Several methods exist today for detecting, counting and identifying microorganisms present in a sample. Most methods entail depositing a portion of the sample in or upon one or more culture media which encourage the growth of the microorganisms. Usually, a different kind of culture medium is used for each type of microorganism of interest. Once the microorganisms have grown on these culture media, further tests are often required to complete their identification. This usually requires the transfer of a portion of the growth to other culture media, in order to determine various important characteristics of the microorganisms (such as the ability to ferment certain sugars, or to grow in the presence of certain chemicals).

These methods are widely used in a number of areas including testing of foods, water and effluent for pathogenic bacteria, spoilage organisms, or bacteria indicative of poor sanitary practices, testing of pharmaceutical products, and testing of urine in the diagnosis of urinary tract infections. Other applications include, for example, the control of starter cultures used in fermentation processes (such as in cheese or yoghurt manufacture and in the production of beers and wines).

The invention will be described with respect to the particular application of the food industry, and it is to be understood that it is not restricted thereto, but is equally applicable to any other industry.

Most microorganisms found in foods are saprophytic. Certain of these, when growing in a food, produce chemical changes resulting in food spoilage. Other saprophytes, due to certain of their characteristics, provide information as to the acceptability of the manufacturing process or the hygienic condition of the processing plant. This group of bacteria is usually referred to as the "indicator organisms". Pathogenic organisms can also be found in foods. Certain of these organisms produce toxins or poisons harmful to man; others, such as Salmonella, cause infections. Government regulations limit the quantity of certain indicator organisms in foods, and prohibit the sale of food products containing certain pathogenic bacteria. For example, the presence of Salmonella is specifically prohibited in numerous foods under the Canadian Food and Drugs Act and Regulations, and Section 4(a) of this Statute prohibits the sale of any food that "has in or upon it any poisonous or harmful substance". Other countries have similar prohibitions.

Microbiological examination of foods provides information concerning the quality of the ingredients and the hygienic conditions under which the food was processed. It can also help to determine the effectiveness of any preservative or sterilizing treatment used in the production of the food. The detection of significant levels of indicator organisms, or example, can signal a breakdown in processing plant hygiene. This finding would lead to an examination of equipment and a review of procedures in order to trace the source of the problem. Corrective measures could then be instituted to prevent a reoccurrence.

Microbiological techniques for food examination are similar to those used in other areas of microbiology. For the most part, they consist of cultural procedures, although direct microscopy and serological procedures are used to some extent. The type of examination performed is determined by the type of food product to be examined and, more importantly, by the type of microorganisms being sought. For example, a food being analyzed for mold contamination would be handled differently from one being examined for Salmonella.

A typical procedure to determine a quantity of a specific group of bacteria in a food sample is as follows. A measured quantity of the food is homogenized in a known volume of a suitable diluent. This homogenate is then diluted in a series of ten-fold steps, the number of dilutions being dependent upon the expected level of the bacteria in question in the sample. A measured volume of at least two of these ten-fold homogenate dilutions is then deposited onto a suitable culture medium, contained in Petri Dishes (The "Dilution Petri Dishes"), and evenly spread over the surface of the medium. Usually, two separate Petri Dishes of medium are used for each of the dilutions being transferred. These Dilution Petri Dishes are incubated to allow the organisms to grow. During incubation, each viable bacterial cell should produce a colony on the surface of the culture medium. After incubation, the analyst places each Dilution Petri Dish under a magnifying lens and counts the number of colonies which have formed. Based on this information, and the extent to which the sample was diluted, the analyst is able to deduce the number of organisms present in the original sample that may belong to the group of bacteria in question (known as the presumptive count).

In order to determine whether all of the bacteria included in the presumptive count do, in fact, belong to the required group, one or more confirming tests are required. To this end, the analyst usually transfers up to ten colonies of bacteria from one of the pairs of Dilution Petri Dishes onto fresh culture medium in Petri Dishes, both to verify the purity of the original colony (that is, to determine that only one type of bacterium was present therein) and to increase the number of cells of the bacterium available for the confirming tests. In order to successfully accomplish this transfer, each colony of bacteria must be individually transported using a suitable implement such as a sterile needle. These dishes are incubated, and the colonies that develop on the surface of the culture medium are then used to inoculate one or more culture media, or to perform other tests (such as serology), depending upon the group of bacteria in question. Following the completion of these tests, the analyst evaluates the results obtained for each of the original colonies meeting the confirmation criteria. This fraction is then multiplied by the presumptive count, to yield the confirmed number of bacteria of the group in question in the original sample (known as the confirmed count).

The confirmation procedure described above has a major drawback in that the decision on the part of the analyst as to which colonies to transfer from the Dilution Petri Dishes for further tests is based in large part on subjective criteria. Since such a small proportion of the colonies are carried through the confirmation procedure (often fewer than 5% of the colonies present on the Dilution Petri Dishes), an erroneous decision on even one of the colonies can have a large impact on the final calculation of the confirmed count.

The field of mutation research is another area requiring the transfer or duplication of a large number of colonies. The Ames test for carcinogenicity, for example, tests the ability of a wide variety of ingredients in foods and pharmaceutical products to cause genetic mutations in bacteria (this has been linked to the potential to cause cancer in man). In this test, a bacterium with known growth properties is subjected to the chemical being tested. The bacterium is then allowed to grow and produce colonies on a culture medium (primary medium) in a Petri Dish. Each of these colonies must be transferred onto a series of different culture media (secondary media) in order to detect any changes in growth patterns (for example, the development of resistance to a particular antibiotic to which the bacterium was previously sensitive). The transfer of the bacterial colonies can presently be performed using one of two methods.

The first method involves transferring individual colonies to the secondary media using a sterile needle or other similar device. This method is slow and tedious. It places severe limitations on both the number of culture media that can be included in the experiment and the number of potential cancer-causing chemicals which can be tested. The second method involves stretching a piece of velvet cloth over a solid block (usually of wood) and securing the cloth in place. The surface of the velvet is sterilized by whatever means are feasible. The surface of the velvet is first applied by hand against the colonies growing on the surface of the primary medium and then manually duplicated onto the surfaces of each of the secondary media. This second procedure, if very carefully applied, permits the simultaneous transfer of a larger number of colonies. However, because it is a totally freehand manual operation, significant problems associated with the accurate transfer of colonies are common. These problems will manifest themselves as incomplete transfers due to insufficient pressure or to smearing of colonies due either to excessive pressure or to lateral hand motion while duplicating.

More recently, a novel apparatus for enumerating microorganisms has been developed. As discussed in U.S. Pat. No. 3,929,583 granted on Dec. 30, 1975 to Canadian Patents and Development Limited, this apparatus comprises a membrane filter capable of retaining microorganisms on its surface when a fluid sample is passed through it. A barrier material is imprinted on the surface of the filter which restricts the spread of colonies through its physical properties. The pattern produced defines a plurality of ordered, microbial colony-isolating cells wherein the cells are usually smaller in area than in normal colony area.

The use of the hydrophobic grid membrane filter (hereinafter referred to as HGMF) has produced a substantial advance in the field of microbiology. The regularity in size, shape and optical density, and the orderly arrangement of colonies as a result of the gridded pattern of barrier material of the HGMF has permitted the replacement of manual counting with optoelectronic scanning, thus saving analyst time and producing more reliable and reproducible results.

Even with the advent of the HGMF, the problem still existed as to how to transfer or duplicate the colonies of microorganisms growing on the HGMF to fresh or different culture media so that further tests could be conducted on the microorganisms from the original sample.

SUMMARY OF THE INVENTION

Accordingly, it is an object of the present invention to at least partially overcome these disadvantages by providing an apparatus which is adapted to duplicate a primary culture of microorganisms to form one or more secondary cultures of microorganisms.

It is a further object of the invention to provide an apparatus adapted to transfer bacteria growing on a hydrophobic grid membrane filter to one or more other hydrophobic grid membrane filters such that each colony of bacteria on the secondary filters occupies the same coordinates as the colony of bacteria occupies on the primary filter.

To this end, in one of its aspects, the invention provides an apparatus for transferring a growth of microorganisms, the apparatus comprising a body and a transfer material on one surface of said body, the transfer material adapted to be brought into contact with a primary medium having a growth of microorganisms on the surface thereof, and to transfer the growth to at least one secondary medium.

In another of its aspects, the invention further provides an apparatus for transferring a growth of bacteria on a hydrophobic grid membrane filter, the apparatus comprising a body and a transfer material on one surface of the body, the transfer material adapted to be brought into contact with a growth of bacteria on the surface of the membrane filter, and to transfer the growth to at least one secondary hydrophobic grid membrane filter on a secondary growth medium, such that each bacterial colony is transferred to the identical co-ordinates on the secondary hydrophobic grid membrane filter as is occupied on the primary filter.

In yet another of its aspects, the invention provides a method of duplicating a growth of microorganisms which comprises contacting a primary growth of microorganisms with a transfer material, then contacting the transfer material with the surface of at least one secondary growth medium.

BRIEF DESCRIPTION OF THE DRAWINGS

Further objects and advantages of the invention will appear from the following description taken together with the accompanying drawings in which.

DESCRIPTION OF THE PREFERRED EMBODIMENTS

The invention will now be described with respect to one preferred embodiment thereof. However, it is understood that variations of its components may occur within the scope of this invention. Some of these alternate embodiments will be referred to subsequent to the description of the following embodiments.

Figure 1:
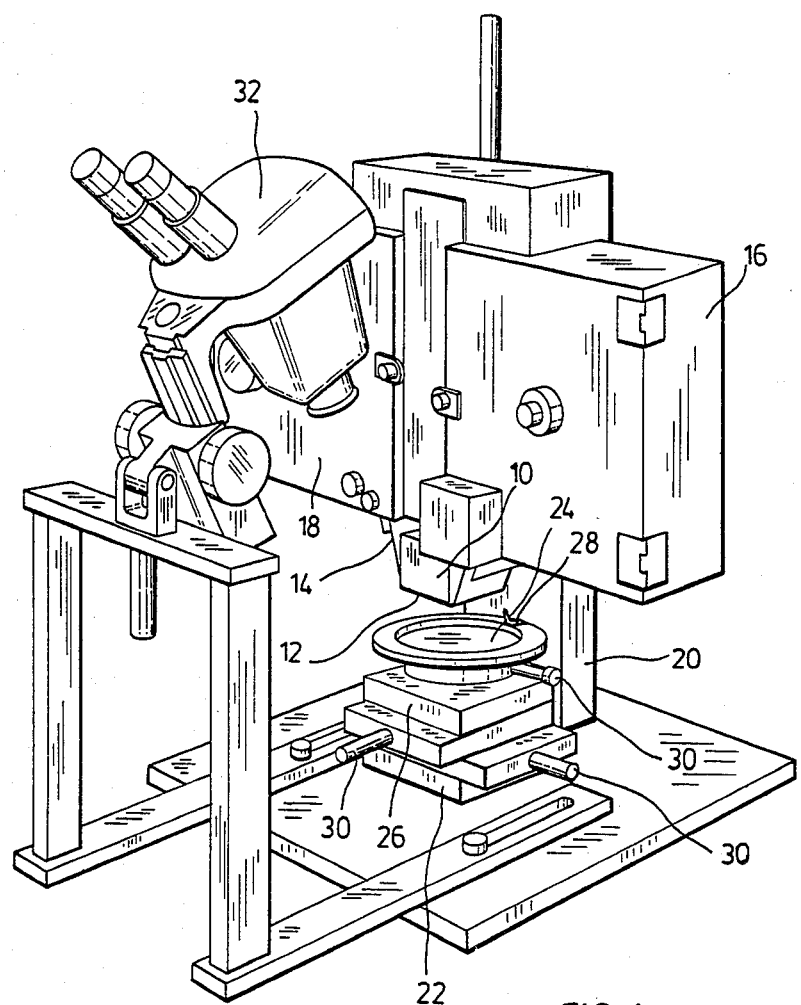
FIG. 1 is a front perspective view of one embodiment of the invention.

Referring first to FIG. 1, there is shown a front perspective view of the components of the transfer apparatus in a preferred embodiment. The apparatus as shown therein, consists essentially of a movable transfer body 10 which has at least one flat surface 12 thereon. A transfer material 14 is fed from a supply reel (not shown) encased in casing 16, around the surface 12 of the body 10 to a take-up reel (not shown) in casing 18. The supply reel may be interchanged with the take-up reel and it is immaterial whether the transfer material is advanced in one direction or in the opposite direction.

The casings 16, 18 and the movable body 10 are all supported on a support stand 20. The support stand 20 also supports a movable platform 22 which has in this embodiment, a circular depression 24 on a mechanical stage 26. The depression 24 is sized so that a Petri dish fits snugly therein. A clip 28 or similar device may also be used to retain the Petri dish in place. Control knobs 30 are provided to adjust the horizontal, vertical and rotational orientation of the platform 22.

A stereomicroscope 32 is provided at the opposite end of the stand 20 such that it will view the top of the Petri dish which is placed in the depression 24 as explained hereinafter.

Figure 2:
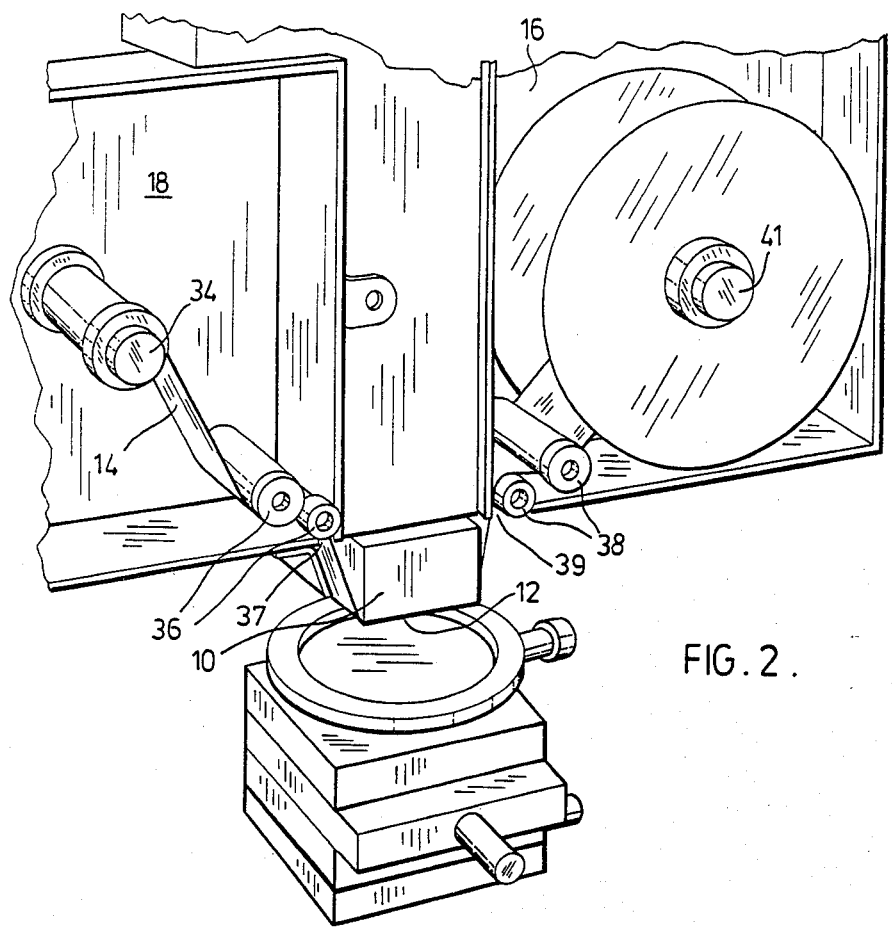
FIG. 2 is a partial view of the feed mechanism for the transfer material of the embodiment shown in FIG. 1.

FIG. 2 shows a partially cut-away view of casing 18 with the transfer material 14 being fed over the body 10 and to the opposite reel.

Material 14 is fed from reel 34 around a pair of guide rollers 36 through a slot 37, then to the surface 12 of the body 10. It is fed across the surface, through slot 39, around guide rollers 38 to the take-up reel 41 in casing 16. It is immaterial whether material 14 is fed from casing 18 to casing 16 or fed from casing 16 to casing 18.

Figure 3:
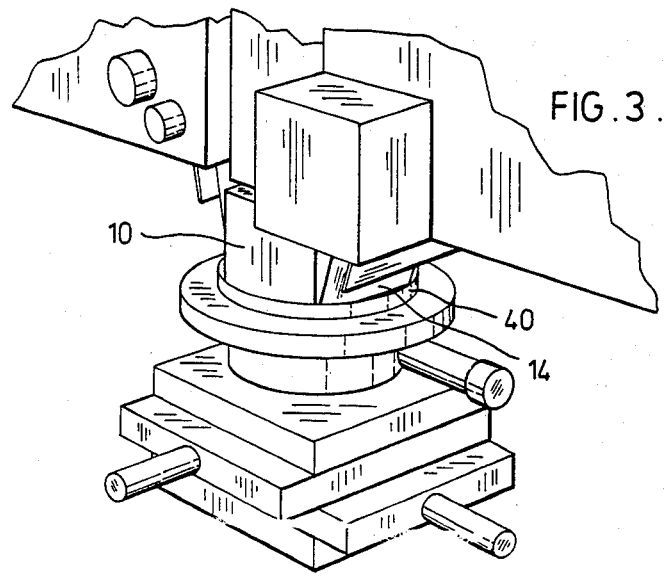
FIG. 3 is an enlarged view of the support body when lowered to contact the primary or secondary medium in a Petri dish.

FIG. 3 shows a partial view of the apparatus when the body 10 is in a lowered position. As shown in FIG. 3, a Petri dish 40 is placed snugly in depression 24 and the transfer material 14 is wound around the surface 12 of the body 10. By means of any suitable adjustment means located on stand 20, the body 10 is lowered into the Petri dish 40 as will be explained hereinafter.

The operation of the apparatus will now be explained. The present apparatus is used to duplicate a growth of microorganisms. First, a primary culture of the microorganisms is grown in a Petri dish 40 or similar container. Once the primary growth has reached a sufficient level, the culture is then duplicated using the present apparatus.

A reel of transfer material 14 is placed either in casing 16 or casing 18 and fed around guide rollers 36, through the slot 37, around surface 12 onto reel 41 in the opposite casing. The Petri dish 40 is then placed in depression 24 and is held securely in place by clip 28.

The operator then orientates platform 22 by means of control knobs 30 to the correct horizontal, vertical and rotational positions so that the body 10 will fit directly into the Petri dish 40, and so that the hydrophobic grid membrane filter (when used) is correctly positioned. The body 10 is then lowered into the position as shown in FIG. 3. The operator views this operation through stereomicroscope 32 equipped with a cross-hair in one eye-piece which aids in aligning the Petri dish 40 and the hydrophobic grid membrane filter with the body 10.

The body 10 is lowered until the transfer material 14 comes into contact with the growth of microorganisms in the Petri dish 40 and then is raised to the "up" position. The original Petri dish 40 is removed and a second dish is put in its place. The body 10 is then lowered until the transfer material 14 touches the medium in the second Petri dish thereby inoculating the second medium with exactly the same microorganisms as were present in the primary medium.

This process is repeated as desired and a number of media may be inoculated with exactly the same pattern of growth of microorganisms as was found in the primary medium.

Various modifications of this device may be made within the spirit and scope of this invention. Some examples of these embodiments are as follows.

The transfer body 10 is shown in FIG. 1 with at least one flat surface 12 thereon. The body 10 may, if desired, have a slightly convex surface instead of flat surface 12. It is, in fact, desirable to have a marginally convex surface as most media used have a marginally concave surface. As a culture media is poured into a suitable receptacle such as a Petri dish, it will flow out towards the edges and take on a slightly concave shape. Thus, the convex surface on the body 10 compensates for this and improves the operation of the device.

The movement of the body 10 may be controlled by several different methods. It is preferred that travel be preset to prevent accidentally lowering or raising the body too far. The movement of the body 10 may be done by manual control or by any suitable means. For example, the device may be spring loaded so that the body will automatically return to the "up" position. The unit itself may be motorized or driven by compressed air.

The travel of the body may also be entirely automated. the body would be lowered until the transfer material touched the medium (either primary or secondary) in the Petri dish when a pressure sensor would then return the body to the "up" position. Also, a light sensitive detector may also be used instead of the pressure sensor.

A further embodiment of this device is that body 10 is stationary and the stage 26 is movable to contact the transfer material. In this embodiment, the stage 26 will move towards and away from the body 10 so that the transfer material 14 comes into contact with the primary and secondary media. The stage 26 may be movable by any well known means and controlled by the operator.

The transfer material 14 may be of any suitable material which can be sterilized. It has been found that a flocked velvet ribbon of an acetate-rayon blend works well. The material should be capable of being sterilized, one suitable means being exposure to dry heat at about 121° C. for several hours.

The transfer material may be any suitable material which has a dense pile and a woven or fused edge. It must be capable of being sterilized by any known method such as moist or dry heat, ethylene oxide treatment, or gamma irradiation, without deterioration. The transfer material is preferably in a roll form in order that it may be continuously used. In other words, once transfer of the growth from one primary medium has been achieved, the knob on the take-up casing is turned thereby advancing the material so that a fresh and clean area of the transfer material is ready to be used for duplicating a second primary medium. This speeds up the process considerably. The knob may be of course replaced by any other suitable device, such as a motorized feed unit to advance the material a pre-set distance.

The control knobs 30 may also be replaced by any conventional means to control the orientation of the platform 22. They may be mechanical or they may be motorized using any well known switches to control the movement thereof. Alternatively, the entire alignment may be electronically controlled using a light sensing device to determine that the HGMF is properly positioned. It is also possible to use a remote placing device where it is desired that the operator's hands not touch any of the components.

While the use of a stereomicroscope 32 as shown in FIG. 1 is preferred, it may be replaced by any suitable viewing system which will allow the operator to view the movement of the Petri dish 40 on the stage 26. A binocular viewing system is preferred since this will allow the operator to see the movement in proper perspective.

Most bacterial cultures are grown on culture media in Petri dishes which are the preferred receptacles. However, any suitable receptacle may be used, as long as the depression 24 is of a corresponding shape. It is to be understood that the depression 24 need not be of a circular shape but it must correspond to the shape of the receptacle in which the primary and/or secondary media are placed.

The present device is most suited to transfer bacteria growing on a Hydrophobic Grid Membrane Filter (HGMF) to a series of other HGMF's in such a way that each colony of bacteria on the primary HGMF occupies the exact same coordinates on all of the resultant or secondary HGMF's.

In this case, a Petri dish containing a primary HGMF is placed by hand in the depression in the mechanical stage. The HGMF is positioned using the horizontal, vertical and rotational control knobs so that the "T" shaped marking located in the border of the HGMF is brought into alignment with a cross-hair in the eyepiece of the stereomicroscope.

The structure and use of the HGMF is explained and disclosed in U.S. Pat. No. 3,929,583 granted to Canadian Patents and Development Limited on Dec. 30, 1975. It comprises a membrane filter element which has a barrier material imprinted on its surface, which restricts the spread of colonies by its physical properties. Thus, a pattern of ordered, microbial colony isolating cells is obtained. The gridded filter facilitates colony detection and counting and makes possible high colony density counts.

By using the device of the present invention, it is now possible to transfer or duplicate the colonies of microorganisms growing on the HGMF to fresh or different culture media so that further tests can be conducted on the microorganisms from the original sample. In addition to the ability to duplicate the colonies of microorganisms, it is particularly important that these colonies of microorganisms may be duplicated in exactly the same growth patterns as in the original HGMF. This has heretofore been impossible to achieve.

Although the disclosure describes and illustrates a preferred embodiment of the invention, it is to be understood the invention is not restricted to this particular embodiment.

What we claim is:

1. An apparatus for transferring a growth of microorganisms, said apparatus comprising:
   a body;
   a transfer material extending across one surface of said body, said transfer material adapted to be brought into contact with a primary medium having a growth of microorganisms on the surface thereof, and to transfer said growth to at least one secondary medium;
   a support stand to support said body;
   a moveable platform for holding and positioning said primary medium supported by said support stand and adapted to be oriented in a predetermined horizontal, vertical and rotational orientation, said moveable platform facing said transfer material such that when said body is moved or said platform is moved, said transfer material contacts said growth of microorganisms;
   a supply reel for supplying the transfer material;
   a take-up reel for taking-up said transfer material; whereby said transfer material moves across the surface of said body when the transfer material is supplied by said supply reel and taken-up by said take-up reel.

2. An apparatus as claimed in claim 1 further including a pair of casings, one casing housing said supply reel and the other casing housing said tape-up reel.

3. An apparatus as claimed in claim 1 wherein said platform has a stage thereon with a depression on the top surface of said stage, said depressions adapted to retain a receptacle therein, said receptacle adapted to retain a growth of microorganisms on the surface thereof.

4. An apparatus as claimed in claim 3 wherein said receptacle is a Petri dish.

5. An apparatus as claimed in claim 3 further including retaining means adapted to retain said receptacle in said depression.

6. An apparatus as claimed in claim 1 further including control means to control the horizontal, vertical and rotational orientation of said platform.

7. An apparatus as claimed in claim 1 further including a viewing system to view the movement of said transfer material.

8. An apparatus as claimed in claim 7 wherein said viewing system is a binocular viewing system.

9. An apparatus as claimed in claim 8 wherein said binocular viewing system is a stereomicroscope.

10. An apparatus as claimed in claim 1 wherein said transfer material is a flocked velvet ribbon of an acetate-rayon blend.

11. An apparatus as claimed in claim 1 wherein said transfer material is sterile.

12. An apparatus as claimed in claim 1 wherein said transfer material has a dense pile and a woven or fused edge.

13. An apparatus as claimed in claim 1 wherein said transfer material is precut squares of material which have been fixed to a rigid backing.

14. An apparatus as claimed in claim 1 wherein said transfer material is said moveable platform.

15. An apparatus for transferring a growth of microorganisms, said apparatus comprising:
(a) a movable body;
(b) a sterile transfer material, adapted to be brought into contact with a primary medium having a growth of microorganisms on the surface thereof, and to transfer said growth to at least one secondary medium, said transfer material having a dense pile and a woven or fused edge, said transfer material extending across one surface of said body;
(c) a supply reel housed in a first casing and a take-up reel housed in a second casing, said supply reel adapted to continuously supply said transfer material across one surface of said body, said take-up reel adapted to take-up said transfer material from said body;
(d) support stand with a platform supported thereon, said platform adapted to be oriented in a predetermined horizontal, vertical and rotational orientation; said platform having a stage thereon with a depression adapted to hold a receptacle containing said primary medium on the top surface of said stage; and
(e) a viewing system to view the orientation of the receptacle relative to the transfer material.

16. An apparatus as claimed in claim 15 wherein said moveable body has at least one flat surface across which the transfer material extends.

17. An apparatus as claimed in claim 15 wherein said movable body has at least one convex surface across which the transfer material extends.

18. An apparatus as claimed in claim 15 wherein said receptacle is a Petri dish.

19. An apparatus as claimed in claim 18 further including a retaining means to retain said Petri dish in said depression.

20. An apparatus as claimed in claim 15 wherein said viewing system is a stereomicroscope.

21. An apparatus as claimed in claim 15 wherein said transfer material is a flocked velvet ribbon of an acetate-rayon blend.

* * * * *